United States Patent [19]

DiMaio et al.

[11] Patent Number: 4,891,358

[45] Date of Patent: Jan. 2, 1990

[54] ANF DERIVATIVES WITH NOVEL BRIDGING

[75] Inventors: John DiMaio, Montreal; Dominik M. Wernic, Laval; Jorge Jaramillo, Dollard des Ormeaux, all of Canada

[73] Assignee: Bio-Mega Inc., Laval, Canada

[21] Appl. No.: 284,555

[22] Filed: Dec. 15, 1988

[30] Foreign Application Priority Data

Dec. 16, 1987 [CA] Canada ................................. 554516

[51] Int. Cl.$^4$ ........................... C07K 7/00; C07K 5/02; C07K 7/08
[52] U.S. Cl. ..................................... 514/13; 530/324; 530/325; 530/326
[58] Field of Search .................. 514/13; 530/324, 325, 530/326

[56] References Cited

U.S. PATENT DOCUMENTS

| | | |
|---|---|---|
| 4,670,540 | 6/1987 | Sakakibara . |
| 4,721,704 | 1/1988 | Chang et al. ........................... 514/11 |
| 4,757,048 | 7/1988 | Lewichi et al. ...................... 530/325 |
| 4,764,504 | 8/1988 | Johnson et al. ........................ 514/12 |

FOREIGN PATENT DOCUMENTS 1243100 10/1986 Japan .

85/04872 11/1985 PCT Int'l Appl. ................... 514/13

OTHER PUBLICATIONS

A. DeBold et al., Life Sciences, 28, 89 (1981).
M. G. Currie et al., Science 221, 71 (1983).
M. Cantin and J. Genest, Endocrine Reviews, 6, 107 (1985).

*Primary Examiner*—Howard E. Schain
*Assistant Examiner*—Susan Learned
*Attorney, Agent, or Firm*—Daniel Reitenbach; Mary-Ellen M. Timbers; Alan R. Stempel

[57] ABSTRACT

Disclosed herein are derivatives of atrial natriuretic peptides wherein the exocyclic N-terminal peptide segment is deleted and the two cysteinyl residues (at positions 105 and 121) of the natural sequence are replaced with a trivalent unit, —NHCH(CO—)—Q—X—Y—CH$_2$CH$_2$CO— wherein Q is methylene, ethylene or CR'R'' wherein R' and R'' each independently is lower alkyl, X is oxy or thio, and Y is methylene or des-Y. The derivatives may be optionally substituted at various positions including positions 106, 107 and 124. The derivatives possess ANF-like activity and are indicated for treating hypertension and for treating pathological conditions resulting from an imbalance of body fluids and electrolytes.

15 Claims, No Drawings

ANF DERIVATIVES WITH NOVEL BRIDGING

FIELD OF INVENTION

This invention relates to atrial peptide derivatives, to processes and intermediates for their production, to pharmaceutical compositions of the derivatives, and to the use of the peptide derivatives as vasorelaxant, diuretic and antihypertensive agents.

BACKGROUND OF THE INVENTION

The mammalian atrium produces a group of peptides known collectively as the atrial natriuretic factor (ANF). The peptides now have been shown to possess potent diuretic, antihypertensive and smooth muscle relaxant properties. Prior to 1981, the existence of this active principle had been only the subject of a proposition. However, in the early part of this decade two pioneering experiments demonstrated the existance and important properties of this factor; namely, A. J. de Bold et al., Life Sciences, 28, 89 (1981) reported that an injection of an extract of rat cardiac atria produced an immediate and potent diuretic response in the rat. Two years later, M. G. Currie et al, Science, 221, 71 (1983) reported that a rat cardiac atria extract possessed potent smooth muscle relaxant activity. Since these reports, a great deal of attention has been directed to the structure elucidation of the substances that comprise ANF, and to investigations of the role ANF in nature's regulation of body fluid volume and blood pressure. For a review of these developments, see M. Cantin and J. Genest, Endocrine Reviews, 6, 107 (1985). Briefly, with reference to the elucidation of the ANF substances, the active principle in the rat atrium has been shown to be derived from a prohormone containing 152 amino acids. In human atrium, a corresponding prohormone containing 151 amino acids has been identified. Subsequent investigations have established that fragments of the prohormones containing from about 20 to 33 amino acids are more potent that the prohormones themselves, provided that the fragments still contain the C-terminus portion and the cyclic structure of the prohormone. The cyclic structure results from an intramolecular disulfide bridge formed between two half cystine residues at positions 105 and 121 of the peptide sequence. An example of such a fragment of the rat prohormone is rat ANF-(101-126) which has the following structure:

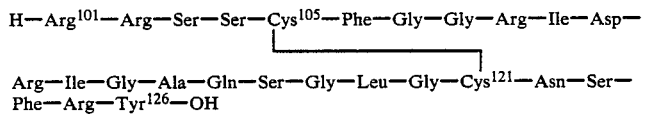

The corresponding fragment of the human prohormone, human ANF-(101-126), has the same structure except for the replacement of the isoleucyl residue at 110 by a methionyl residue.

Chemists now have synthesized the smaller, more active peptides (i.e. fragments) thus making them readily available for extensive biological investigations and for possible development as diuretic and antihypertensive agents. However, the development of the natural peptides is hampered by their rapid decomposition in vivo by enzymatic processes. Accordingly several investigators are now looking at derivatives or analogs of the natural atrial peptides as a source for potential drugs with improved stability, potency and/or duration of action over the natural peptides. For example, see J. Rivier and F. Edouard, PCT patent application W085/04872, published Nov. 7, 1985; Japanese patent application No. 61243100, published Oct. 29, 1987, and S. Sakakibara, U.S. Pat. No. 4,670,540, issued June 2, 1987. The present application discloses new atrial peptide derivatives having a favorable biological profile which renders them useful as antihypertensive agents and for the treatment of pathological conditions resulting from an imbalance of body fluids and/or electrolytes.

SUMMARY OF THE INVENTION

The atrial peptide derivatives of this invention are represented by formula 1

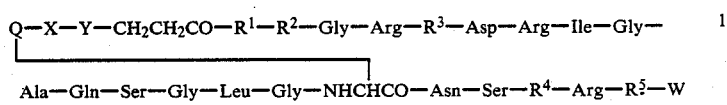

wherein
Q is methylene, ethylene or CR'R" wherein
R' and R" each independently is a or lower alkyl;
$R^1$ and $R^4$ each independently is Phe, 2FPhe, 3FPhe, 4FPhe, $2CF_3Phe$, $3CF_3Phe$ or $4CF_3Phe$;
$R^2$ is Gly, Ala or D-Ala;
$R^3$ is Ile or Met;
$R^5$ is Tyr or des-$R^5$;
X is oxy or thio;
Y is methylene or des-Y; and
W is hydroxy, lower alkoxy, amino or lower alkylamino;
with the proviso that when Q is CR'R" as defined herein, then X is thio; or a therapeutically acceptable salt thereof.

A preferred group of the peptide derivatives of this invention is represented by formula 1 wherein Q, $R^2$, $R^3$, $R^5$, X and Y are as defined hereinabove, $R^1$ and $R^4$ each independently is Phe, 2FPhe, 3FPhe or 4FPhe, and W is hydroxy, lower alkoxy or amino; or a therapeutically acceptable salt thereof.

A more preferred group of the peptide derivatives is represented by formula 1 wherein Q is methylene, ethylene or $C(CH_3)_2$, $R^1$ and $R^4$ each independently is Phe, 2FPhe or 4FPhe, $R^2$, $R^3$ and $R^5$ are as defined hereinabove, X is thio, Y is methylene or des-Y, and W is hydroxy or lower alkoxy; or a therapeutically acceptable salt thereof.

A most preferred group of the peptide derivatives is represented by formula 1 wherein Q is methylene or $C(CH_3)_2$, $R^1$ and $R^4$ each independently is Phe, 2FPhe, or 4FPhe, $R^2$, $R^3$ and $R^5$ are as defined hereinabove, X is thio, Y is methylene and W is hydroxy or methoxy; or a therapeutically acceptable salt thereof.

Included within the scope of this invention is a pharmaceutical composition comprising a peptide derivative of formula 1, or a therapeutically acceptable salt thereof, and a pharmaceutically acceptable carrier.

Also included within the scope of this invention is a method of effecting a vasorelaxant, diuretic, or antihypertensive response in a mammal which comprises administering to the mammal in need of the response a therapeutically effective amount of a peptide derivatives of formula 1, or a therapeutically acceptable salt thereof.

Processes for preparing the peptide derivatives of formula 1 are described hereinafter.

DETAILS OF THE INVENTION

For convenience, the peptide derivatives of this application hereinafter are designated simply as peptides.

The term 'residue' with reference to an amino acid means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commission on Biochemical Nomenclature, see Biochemistry, 11, 1726–1732 (1972). For instance, Met, Met(O), Gln, Ala, Gly, Ile, Arg, Asp, Phe, Ser, Leu, Cys, Asn, and Tyr, hCys and hSer represent the 'residues' of L-methionine, L-methionine sulfoxide, L-glutamine, L-alanine, glycine, L-isoleucine, L-arginine, L-aspartic acid, L-phenylalanine, L-serine, L-leucine, L-cysteine, L-asparagine, L-tyrosine, L-homocysteine and L-homoserine, respectively. D-Ala represents the represents the residue of D-alanine. Pen represents the residue of L-penicillamine.

The symbol "2FPhe" represents the 'residue' 2-fluoro-L-phenylalanyl, i.e. (S)-α-amino-(2-fluorobenzene)propanoyl. Similarly, 3FPhe, 4FPhe, 2CF$_3$Phe, 3CF$_3$Phe and 4CF$_3$Phe represent the residues 3-fluoro-L-phenylalanyl, 4-fluoro-L-phenylalanyl, 2-(trifluoromethyl)-L-phenylalanyl, 3-(trifluoromethyl)-L-phenylalanyl and 4-(trifluoromethyl)-L-phenylalanyl, respectively.

According to the convention used to designate ANF peptides in an abbreviated form, the sequence of the amino acid residues therein is indicated by setting forth the position numbers of the first and last amino acid residues of the sequence in parenthesis following the term "ANF". The particular species (e.g. human or rat) from which the sequence is derived, is expressed by a prefix. Thus, the ANF peptide of rat origin with a free C-terminal carboxyl, composed of the 28 amino acid sequence at the C-terminal, is designated as "rat ANF-(99-126)" and the corresponding peptide with a C-terminal primary amide is designated as "rat ANF-(99-126)NH$_2$." ANF derivatives in which particular amino acid residues have been replaced by different residue are indicated by setting forth the symbol for the replacement in parenthesis before the term "ANF", thus, rat [Ala$^{107}$]ANF-(99-126) indicates the corresponding derivative of rat ANF-(99-126) in which the Gly at position 107 is replaced by Ala. With reference to a peptide of the present invention, rat [(CH$_2$CH$_2$CH$_2$CO)$^{105}$]ANF-(105-126)OCH$_3$ indicates the methyl ester of the corresponding rat ANF-(105-126) in which the Cys at position 105 is replaced by the radical CH$_2$CH$_2$CH$_2$CO, the terminal methylene of the radical being bonded to the S of the cysteinyl residue at position 121 and the carbonyl of the radical forming an amide linkage with the amino of the phenylalanyl residue at position 106.

The term "lower alkyl" as used herein means alkyl radicals containing one to three carbon atoms and includes methyl, ethyl, propyl and 1-methylethyl.

The term 'lower alkoxy' as used herein means straight chain alkoxy radicals containing one to six carbon atoms and branched chain alkoxy radicals containing three to six carbon atoms and includes methoxy, ethoxy, propoxy, 1-methylethoxy, butoxy and 2,2-dimethylpropoxy.

The term 'lower alkylamino' as used herein means alkylamine radicals containing one to three carbon atoms and includes methylamino, ethylamino, propylamino and 1-methylethylamino.

The term 'pharmaceutically acceptable carrier' as used herein means a non-toxic, generally inert vehicle for the active ingredient which does not adversely affect the ingredient.

The term 'coupling agent' as used herein means an agent capable of effecting the dehydrative coupling of an amino acid or peptide free carboxy group with a free amino group of another amino acid or peptide to form an amide bond between the reactants. The agents promote or facilitate the dehydrative coupling by activating the carboxy group. Descriptions of such coupling agents and activated groups are included in general textbooks of peptide chemistry, for instance, E. Schroder and K. L. Lubke, "The Peptides", Vol 1, Academic Press, New York, N. Y., 1965, pp 3–128, and K. D. Kopple, "Peptides and Amino Acids", W. A. Benjamin, Inc., New York, N.Y., 1966, pp 33–51. Examples of coupling agents are thionyl chloride, diphenylphosphoryl azide, dicyclohexylcarbodiimide, N-hydroxysuccinimide, or 1-hydroxybenzotriazole in the presence of dicyclohexylcarbodiimide.

The peptides of formula 1 can be prepared by processes which incorporate therein methods commonly used in peptide synthesis such as classical solution coupling of amino acids and/or peptide fragments, and if desired solid phase techniques. Such methods are described for example, by E. Schroder and K. Lubke, cited above, and in the textbook series, "The Peptides: Analysis, Synthesis, Biology", E. Gross et al., Eds., Academic Press, New York, N.Y., 1979–1987, Volumes 1 to 8.

A conventional and practical preparation of the peptides of formula 1 involves using a starting material which ultimately provides the segment for the unique bridging unit of the peptides, i.e. the trivalent unit —NHCH(CO—)—Q—X—Y—CH$_2$CH$_2$CO— wherein Q, X and Y are as defined herein. The ramaining (peptidyl) segment of the final product is elaborated by joining three peptidyl fragments to the starting material whereby a branched intermediate with three side arms is obtained; followed by joining the termini of two of the side arms of the branched intermediate to provide the cyclic structure of the final products.

The key starting material for the present process is represented by formula 2

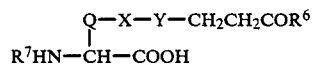

wherein R$^6$ is a carboxyl protecting group, R$^7$ is an amino protecting group, and Q, X and Y are as defined hereinabove. For the presently embodied process, $R^7$ is a protecting group which can be selectively removed in the presence of the protecting group $R^6$. Preferably, $R^6$ is 9-fluorenylmethyl (FmO) or 2,2,2-trichloroethoxy, and $R^7$ is t-butyloxycarbonyl (Boc). The starting material of formula 2 is prepared readily by known methods. For example, the preparation of a preferred starting material of formula 2 in which $R^6$ is FmO, $R^7$ is Boc, Q is methylene, X is thio and Y is methylene is described hereinafter in Examples 1 to 3. A preferred starting material of formula 2 in which $R^8$ is FmO; $R^9$ is Boc, Q is methylene, X is oxy and Y is methylene can be prepared by the process illustrated schematically as follows:

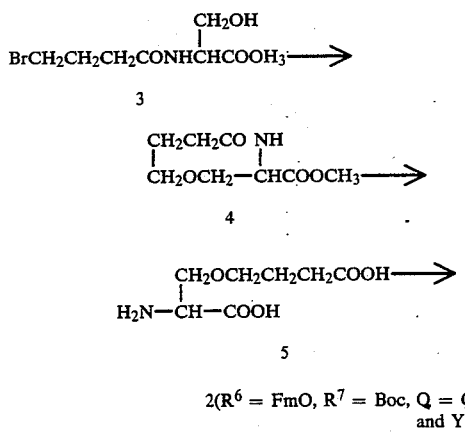

$2 (R^6 = FmO, R^7 = Boc, Q = CH_2, X = O$ and $Y = CH_2)$

With reference to the proceeding process, the ester of formula 3, obtained by coupling L-serine methyl ester with 4-bromobutanoic acid using dicyclohexylcarbodiimide/1-hydroxybenzyotriazole as the coupling agent, is cyclized with sodium hydride to the cyclic lactam of formula 4. Hydrolysis of the latter compound with hydrochloric acid affords the amino-dicarboxylic acid of formula 5. Thereafter, the latter compound is transformed to the desired starting material of formula 2 by introducing the FmO group at the ω-carboxyl group of the amino dicarboxylic acid of formula 5, while the α-amino carboxylic portion is temporarily masked as an oxazolidinone group, see the method of H. Farkasova and J. Rudinger, Coll. Czech. Chem. Commun., 30, 3117 (1965), followed by introduction of Boc to protect the amino group as the last step.

The preferred starting material of formula 2 in which $R^6$ is FmO, $R^7$ is Boc, Q is ethylene, X is oxy and Y is des-Y can be prepared by a process analogous to the preceding process using the ester obtained by coupling L-homoserine and 3-bromopropionic acid as the starting material.

The preferred starting material of formula 2 in which $R^8$ is FmO, $R^9$ is Boc, Q is ethylene, X is thio and Y is des-Y can be prepared by reacting L-homocystine with 3-bromoproponic acid in the presence of sodium/ammonia to obtain S-[3-fluorenylmethoxy)-3-oxopropyl]-L-homocysteine, followed by reacting the latter compound with di-t-butyl dicarbonate to introduce Boc as the amino protecting group.

As noted before, the peptides of formula 1 are elaborated by sequentially attaching three sidearms, i.e. peptidyl fragments, to the framework or bridging unit provided by the starting material 2, to give a branched intermediate with one N-terminal sidearm and two C-terminal sidearms. Thereafter, the branched intermediate is intramolecularly coupled (i.e. the termini of the two appropriate sidearms thereof, one having a C-terminus and the other a N-terminus, are joined) to afford the cyclic framework of the final product. The remaining sidearm thus becomes the exocyclic C-terminal segment of the final product.

The embodied process for this elaboration is characterized by:

(a) stepwise joining of peptidyl fragments to a series of intermediates, beginning with the starting material of formula 2, so that ultimately the desired sequence of amino acids of the final product is provided;

(b) using a protecting group on a carboxyl which can be selectively removed in the presence of other protecting groups on an intermediate when that carboxyl is destined for the coupling reaction to follow;

(c) using an amino protecting group for the N-terminal sidearm which can be selectively removed in the presence of other protecting groups on the intermediate prior to the intramolecular coupling of the two appropriate sidearms to form the cyclic framework for the final product;

(d) protecting amino acid residue sidearm functional groups, which might otherwise interfere with a reaction step, with groups which can be removed after the cyclic framework of the final product has been elaborated;

(e) and when the terminal carboxyl of the sidearm having the sequence of amino acids of the exocyclic C-terminal segment of the final product is present, protecting that carboxyl with a protecting group which can be removed after the cyclic framework of the final product has been elaborated.

The embodied process can be represented schematically as follows:

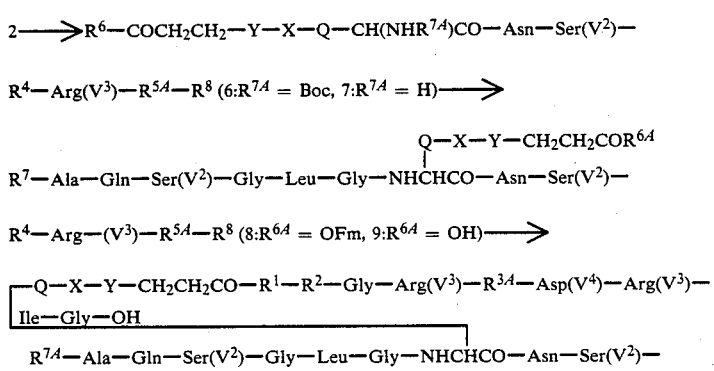

$R^4-Arg(V^3)-R^{5A}-R^8$ (10:$R^{7A}$ = Boc, 11:$R^{7A}$ = H) 

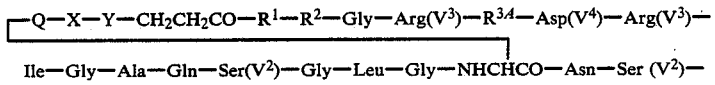

$R^4-Arg(V^3)-R^{5A}-R^8$ (12) 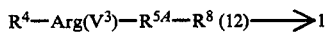1 wherein Q, $R^1$, $R^2$, $R^4$, $R^6$, $R^7$, X and Y (as well as $R^3$ and $R^5$, implicit of formula 1) are as defined hereinbefore, $R^8$ is O-V wherein V is a carboxyl protecting group (preferably benzyl, cyclohexyl or 2,6-dichlorobenzyl), lower alkoxy, amino or lower alkylamino, $R^{3A}$ is Ile, Met or Met(O), $R^{5A}$ is des-$R^{5A}$ or Tyr($V^1$) wherein $V^1$ is a protecting group for the hydroxyl of Tyr (preferably benzyl), $R^{6A}$ is OFm or H, $R^{7A}$ is Boc or H, $V^2$ is a protecting group for the hydroxyl of Ser (preferably benzyl), $V^3$ is a protecting group for the guanidino group of Arg (preferably tosyl or nitro), and $V^4$ is a protecting group for the ω-carboxyl of Asp selected from the group of cyclohexyl and cyclopentyl.

With reference to the preceding schematic representation, the starting material of formula 2 is coupled with the pentapeptide H-Asn-Ser($V^2$)-$R^4$-Arg($V^3$)-$R^{5A}$-$R^8$ wherein $R^4$, $R^8$, $R^{5A}$, $V^2$ and $V^3$ are as defined herein, by means of a coupling agent, to give the corresponding intermediate of formula 6. The latter compound is subjected to the selective removal of the amino protecting group (Boc) to give the intermediate of formula 7 (representing the starting material with the first sidearm attached). Next, the intermediate of formula 7 is coupled with the hexapeptide $R^7$-Ala-Gln-Ser($V^2$)-Gly-Leu-Gly-OH in which $R^7$ and $V^2$ are as defined herein, by means of a coupling agent, to give the corresponding intermediate of formula 8. Subsequent removal of the carboxyl protecting group (FmO) from the latter compound yields the intermediate of formula 9 (representing the starting material with two sidearms attached). The latter compound is transformed into intermediate 10 by coupling the appropriate fragment or series of fragments. Selective removal of the amino protecting group (Boc) gives the branched intermediate of formula 11 (representing the starting material with three sidearms attached). The branched intermediate is cyclized with a coupling agent (intramolecular coupling) to give the cyclic intermediate of formula 12. Subsequent deprotection of the latter compound, namely removal of the remaining protecting groups (V, $V^1$ if present, $V^2$, $V^3$ and $V^4$) in the presence of hydrogen fluoride, affords the corresponding peptide of formula 1 in which W is hydroxyl, lower alkoxy, amino or lower alkylamino.

The peptide of formula 1 of this invention can be obtained in the form of therapeutically acceptable salts.

In the instance where a particular peptide has a residue which functions as a base, examples of such salts are those with organic acids, e.g. acetic, lactic, succinic, benzoic, salicyclic, methanesulfonic or p-toluenesulfonic acid, as well as polymeric acids such as tannic acid or carboxymethyl cellulose, and salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chem. Acta, 43, 1849 (1960).

In the instance where a particular peptide has one or more free carboxy groups, example of such salts are those with the sodium, potassium or calcium cations, or with strong organic bases, for example, triethylamine or N-ethylmorpholine.

In general, the therapeutically acceptable salts of the peptides of formula 1 are biologically fully equivalent to the peptides themselves.

The relaxant effect of the peptides of formula 1 on arterial smooth muscles (vasorelaxant effect), as well as their diuretic, or antihypertensive effect, can be demonstrated in standard pharmacological tests.

For example, the vasorelaxant activity of the peptides of formula 1 can be demonstrated by means of the rat aorta assay. In this instance, the descending thoracic aorta was excised from New Zealand albino rabbits and placed in Krebs solution at room temperature. The composition of this solution was (g/l): NaCl, 6.9; KCl, 0.35; $CaCl_2 \cdot 2H_2O$, 0.7; $MgSO_4 \cdot 7H_2O$, 0.29; $NaHCO_3$, 2.1; $KHPO_4$, 0.16; D-glucose, 2.0. The solution was bubbled with 5% carbon dioxide in oxygen (V/V) to maintain its pH at 7.4. The excised aorta was cleaned of extraneous tissue and cut transversely to obtain six 4 mm wide rings. The rings were mounted vertically according to the method described by C. S. Hooker et al., Blood Vessels, 14, 1 (1977). Essentially, a ring was slipped on two stainless steel (0.4 mm diam. wire) 'L' - shaped supports. The lower one was attached to a fixed tissue holder. The upper support was tied by a thread to a force transducer (Model FT. 03, Grass Instruments, Quincy, Mass, USA) connected to a polygraph for isometric recording of tension. By raising the transducer, the ring was placed under tension and then was readjusted, as the tissue relaxed, until a stable 10 g resting tension was attained. During this equilibration period lasting 30 to 45 minutes, the rings were superfused with Krebs solution warmed so that the temperature of the superfustate was 37° to 38° C. when it reached the tissue. The rate of superfusion was set at 15 ml/minute using a multichanneled peristaltic pump. For the rest of the assay, phenylephrine HCl (Sigma Chemical, St. Louis, Mo., U.S.A.) was added to the superfusate at a concentration of $1 \times 10^{-7}$M. In control experiments this concentration of phenylephrine caused an increase in tension in the rings corresponding to 40 to 60% of their maximal response. This induced increase in tension was maintained throughout the duration of the assay.

The assay was carried out by adding to the tricking superfusate, 3 to 4 cm above an aortic ring, 50 μl of solution of the desired concentration of the test compound. Several doses were administered in increasing order of concentration; at least three of the selected doses caused 15 to 85% relaxation of the tissue. The percent relaxation caused by these doses in the six rings from each rabbit was averaged and the regression line calculated. Four rabbits were used for the assay. The dose of the test compound causing a relaxation equal to 50% (EC50) of the phenylephrine-induced tension was determined from each of the five linear dose-response regressions. The EC50's were averaged and this value, along with its standard error (S.E.M.), was considered an estimate of the potency of test compound. The duration of action (in minutes) was measured from the onset of action to 50% recovery as indicated by the EC50 value.

The results obtained with certain peptides of formula 1 are shown in Table 1. For comparison, the results obtained with the known ANF-(103-126), atriopeptin III (P. Needlemann, U.S. Pat. No. 4,496,544, Jan. 29, 1985) are included in the table.

TABLE I
RABBIT AORTA ASSAY

| PEPTIDE[a] | EC$_{50}$, moles/50 $\mu$l[b] 50 ul |
|---|---|
| rat[(CH$_2$CH$_2$CH$_2$CO)$^{105}$]-ANF(105-126) | 2.6 ± 0.50 × 10$^{-10}$ |
| rat[(CH$_2$CH$_2$CH$_2$CO)$^{105}$]-ANF(105-126)OCH$_3$ | 1.4 ± 0.10 × 10$^{-10}$ |
| rat[(CH$_2$CH$_2$CH$_2$CO)$^{105}$,Pen$^{121}$]-ANF(105-126) | 6.8 ± 0.70 × 10$^-$ |
| rat[(CH$_2$CH$_2$CO)$^{105}$,hCys$^{121}$]-ANF(105-126) | 3.5 ± 0.30 × 10$^{-10}$ |
| Atriopeptin III | 1.9 ± 0.02 × 10$^{-10}$ |

[a]all doses are based on peptide content.
[b]mean of at least 3 determinations ± SEM The diuretic activity of the peptides of, this invention can be demonstrated in vivo in the experimental mental model employing the conscious normotensive rat in a diuretic assay. More explicitly, normotensive male rats (300-325 g) were anesthetized with halothane. Following an application of lidocaine 2% solution, the femoral artery was cannulated for measurements of blood pressure and heart rate, and the femoral vein was cannulated for the administration of the test compounds. The bladder was also cannulated to measure urine flow. After surgery was completed, the animals were placed in restraining cages and allowed to recover from anesthesia for a period of one hour. A Ringer's solution infusion was started at a rate of 1.2 ml per hour. Three control urine samples were collected at 10 minute intervals. The test compound was then infused at a rate varying from 0.5 to 3 $\mu$g/kg/min over 30 minutes. Three test samples of urine were collected at 10 minute intervals during the compound infusion. After the test compound had been infused for 30 minutes and 3 more urine samples were collected. The volume of each urine sample was determined and the electrolyte concentration was measured using a biomedical electrolyte analyser. The animals served as their own controls. The systolic and diastolic blood pressures and the heart rate were determined during each urine collection period.

Table II illustrates the results obtained in the preceding test with exemplified peptides. Artriopeptin III is included for comparative purposes.

TABLE II
DIURETIC ASSAY

| COMPOUND 0.5 $\mu$g/kg/min | URINE VOLUME | ELECTROLYTE EXCRETION[c] | | |
|---|---|---|---|---|
| | | Na$^+$ | K$^+$ | Cl$^-$ |
| rat[(CH$_2$CH$_2$CH$_2$CO)$^{105}$]-ANF(105-126) | 2.8 | 34.0 | 10.2 | 41.1 |
| rat[(CH$_2$CH$_2$CH$_2$CO)$^{105}$]-ANF(105-126)OCH$_3$ | 3.4[d] | 38.1 | 23.5 | 52.1 |
| rat[(CH$_2$CH$_2$CH$_2$CO)$^{105}$,Pen$^{121}$]-ANF(105-126) | 3.0 | 17.9 | 24.8 | 39.6 |
| rat[(CH$_2$CH$_2$CO$^{105}$,hCys$^{121}$]-ANF(105-126) | 1.7 | 7.2 | 3.5 | 15.9 |
| Atriopeptin III | 2.7 | 79.6 | 23.0 | 98.5 |

[a]doses based on peptide content
[b]ratio of treated over control; volume in 10 minute sample (average of three consecutive samples)
[c]treated minus controls, average of three samples
[d]diuretic effect more prolonged than with atriopeptin III The peptides of formulae 1 are indicated for the relief of hypertension and for treating pathological conditions associated with an imbalance of body fluids and/or electrolytes; including for example, edematous conditions resulting from congestive heart failure, pregnancy toxemia and cirrhosis of the liver.

When the peptides of this invention, or their therapeutically acceptable salts, are employed as vasorelaxant, diuretic, natriuretic or antihypertensive agents, they usually are administered systemically to warm-blooded animals, e.g. humans, horses or dogs, in combination with pharmeceutical acceptable carriers, the proportion of which is determined by the solubility and chemical nature of the peptide, chosen route of administration and standard biological practice.

For systemic administration, the peptides of formula 1 are administered by either intravenous, subcutaneous or intramuscular injection, in compositions with pharmaceutically acceptable vehicles or or carriers. For administration by injection, it is preferred to use the peptides in solution in a sterile aqueous vehicle which may also contain other solutes such as buffers or preservatives as well as sufficient quantities of pharmaceutically acceptable salts or of glucose to make the solution isotonic.

Examples of suitable excipients or carriers are found in standard pharmaceutical texts, e.g. in "Remington's Pharmaceutical Sciences", 16th ed, Mack Publishing Company, Easton, Penn., 1980.

The dosage of the peptides will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the peptides of this invention are most desirably administered at a concentration level that will generally afford effective smooth muscle relaxation, without causing any harmful or deleterious side effects. Usually, the peptide of formula 1 is administered at a dose of 0.01 meg to 50 meg per kilogram of body weight per day, although the aforementioned variations will occur. However, a dosage level that is in the range of from about 0.05 meg to 10 meg per kilogram of body weight per day is most desirably employed in order to achieve effective results.

The following examples illustrate further this invention. Solution percentages or ratios express volume to volume relationship. Abbreviations used in the examples include Boc: t-butyloxycarbonyl; Bzl: benzyl; CH$_2$Cl$_2$: methylene chloride; Chxl: cyclohexyl; DDC: N,N'-dicyclohexylcarbodiimide; DIEA: diisopropylethylamine; DMF: dimethylformamide; DPPA: diphenylphosphoryl azide; Et$_2$O: diethyl ether; ethanol; FmO: 9-fluorenylmethyloxy; HOBt: 1-hydroxy-benzotriazole; MeOH: methanol; ONp: 4-nitrophenoxy; Tos: tosyl.

EXAMPLE 1

4-Bromobutanoic Acid 9-Fluorenylmethyl Ester

DDC (6.00 g, 29 mmol) was added in one portion to a cooled solution (0° C.) of 4-bromobutyric acid (5.00 g, 29.9 mmol), 4-(dimethylamino)pyridine (353 mg, 2.9 mmol) and 9-fluorenemethanol (5.63 g, 25 mmol) in CH$_2$Cl$_2$ (150 mL). The mixture was allowed to stand at 4° C. for 18 h, and then filtered. The filtrate was evaporated to dryness under reduced pressure. The residue was dissolved in EtOAc and the solution washed sequentially with 1N NaHCO$_3$, 1N HCl and H$_2$O. The solution was dried (Na$_2$SO$_4$) and evaporated to dryness under reduced pressure. The residue was purified by flash chromatography on silica gel (200 g) using hexane-EtOAc (15:1) as the eluant to give the pure title compound as an oil (7.5 g).

EXAMPLE 2

S-[4-(9-Fluorenylmethoxy)-4-oxobutyl]-L-cysteine

The title compound of example 1 (3.0 g, 8.72 mmol) was added to a solution of L-cysteine (1.0 g, 8.26 mmol) and DIEA (4.4 mL, 24.7 mmol) in EtOH-H$_2$O (1:1, 100 mL). The resulting heterogeneous mixture was stirred vigorously at room temperature (20°–22° C.) for 18 h. The mixture was rendered acidic by the addition of 1N HCl (ph=6). The solid in the reaction mixture was collected on a filter and washed with H$_2$O and EtOH. A suspension of the solid in EtOH (70 mL) was heated with stirring then allowed to cool. The solid in the suspension was collected on a filter, washed with EtOH, Et$_2$O and dried to give the title compound (1.2 g).

EXAMPLE 3

N-(t-Butyloxycarbonyl)-S-[4-(9-fluorenylmethoxy)-4-oxobutyl]-L-cysteine (2:Q=CH$_2$, R$^6$=FmO, R$^7$=Boc, X=S and Y=CH$_2$)

Di-t-butyl dicarbonate (2.18 g, 10 mmol) was added to a solution of the title compound of Example 2 (1.9 g, 4.9 mmol) in 100 ml of dioxane-H$_2$O (1:1) containing DIEA (2.64 mL). The mixture was stirred at room temperature for 18 h, then diluted with H$_2$O (50 mL) and extracted with Et$_2$O. The aqueous phase was made acidic with solid citric acid and then extracted with EtOAc. The combined organic extracts were washed with 1N HCl and then H$_2$O, dried (Na$_2$SO$_4$), and evaporated to dryness to give the title compound as an oil (1.6 g).

EXAMPLE 4

Pentapeptide H-Asn-Ser(Bzl)-Phe-Arg(Tos)-Tyr-(Bzl)-OCH$_3$ (a) Dipeptide Boc-Arg(Tos)-Tyr(Bzl)-OCH$_3$: A solution of Boc-Arg(Tos)-OH (2.14 g, 5 mmol) and DPPA (1.37 g, 5 mmol) in DMF (100 mL) was cooled to −5° C. DIEA (2.6 mL, 15 mmol) and HCl.H-Tyr(Bzl)-OCH$_3$ (1.44 g, 4.5 mmol) were added, each in one portion, to the cooled solution. The solution was stirred at −10° C. for 2h, allowed to stand at 4° C. for 18h, and then evaporated to dryness. The residue was dissolved in EtOAc (75 mL). The solution was washed sequentially with H$_2$O, 1N HCl, 5% aqueous NaHCO$_3$ and H$_2$O, dried, and evaporated to dryness. The residue was dissolved in EtOAc. Addition of Et$_2$O caused an oil to separate from the solution. The mixture was cooled (0° C.) and triturated. The solvent phase of the mixture was removed by decantation. Et$_2$O was added to the residue. After warming the mixture, the preceding trituration and decantation treatment was repeated. Finally, the product was dried under reduced pressure to yield Boc-Arg(Tos)-Tyr(Bzl)-OCH$_3$ (5.3 g).

(b) Dipeptide H-Arg(Tos)-Tyr(Bzl)-OCH$_3$: A solution of the latter product (5.0 g) in CH$_2$Cl$_2$ (50 mL) was cooled (0° C.), TFA (20 mL) was added dropwise to the cooled solution. The reaction mixture was stirred at 0° C. for 45 min, and then at room temperature for 15 min. The mixture was evaporated to dryness. The residue was triturated with Et$_2$O. After removal of the Et$_2$O, the residue was dissolved in MeOH and the resultant solution evaporated under reduced pressure. The residue was treated with Et$_2$O and the mixture was allowed to stand. The resultant solid was collected to give TFA.H-Arg(Tos)-Tyr(Bzl)-OCH$_3$ (5.0 g).

(c) Tetrapeptide H-Ser(Bzl)-Phe-Arg-Tyr(Bzl)-OCH$_3$: The dipeptide of paragraph (b) was used as the starting material, and the coupling step and the deblocking step (i.e. the removal of the Boc) of paragraphs (a) and (b), respectively, were repeated two more times, using serially Boc-Phe-OH and Boc-Ser-(Bzl)-OH as coupling reactants to obtain the desired tetrapeptide.

(d) Title compound of this example: The tetrapeptide of paragraph (c) (2.6 g) was dissolved in DMF (75 mL). DIAE (1.3 mL) and Boc-Asn-ONp (1.0 g) were added to the solution. After 2 h at room temperature, the reaction mixture was evaporated to dryness. The residue was dissolved in EtOAc (100 mL). The solution was washed sequentially with H$_2$O, 1N HCl, 5% aqueous NaHCO$_3$ and H$_2$O, dried and evaporated to dryness. Et$_2$O was added to the residue. The resultant solid was collected by filtration to give the Boc-Asn-Ser(Bzl)-Phe-Arg(Tos)-Tyr(Bzl)-OCH$_3$ (2.0 g). The latter product (1.6 g) was deblocked with TFA according to the procedure of above paragraph (b) to give the desired pentapeptide, i.e. title compound of this example, as the TFA addition salt (1.5 g).

EXAMPLE 5

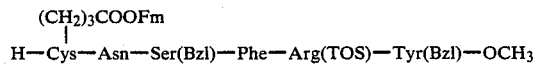
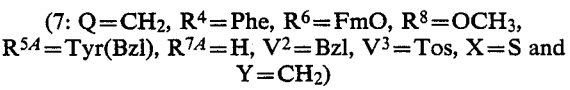

(7: Q=CH$_2$, R$^4$=Phe, R$^6$=FmO, R$^8$=OCH$_3$, R$^{5A}$=Tyr(Bzl), R$^{7A}$=H, V$^2$=Bzl, V$^3$=Tos, X=S and Y=CH$_2$)

A solution of the title compound of Example 3 (631 mg, 1.3 mmol) the title compound of Example 4 (1.0 g, 0.9 mmol) and HOBt (175 mg, 1.3 mmol) in DMF (10 mL) was neutralized to pH 7 by the dropwise addition of DIEA. The solution was diluted with CH$_2$Cl$_2$ (50 mL). Thereafter, DCC (288 mg, 1.4 mmol) was added to the solution in one portion. The reaction mixture was stirred at room temperature for 18 h and then evaporated to dryness under reduced pressure. The residue was suspended in EtOAc (150 mL). The resultant solid was collected on a filter and washed extensively with EtOAc, then with Et$_2$O, and dried to give FmO-CO-(CH$_2$)$_3$-SCH$_2$CH(NHBoc)-CO-Asn-Ser(Bzl)-Phe-Arg(Tos)-Tyr(Bzl)-OCH$_3$ (1.2 g).

The latter compound (1.1 g) was suspended in CH$_2$Cl$_2$ (25 mL). At room temperature, the suspension was treated dropwise with TFA (20 mL) and then stirred for 45 min. Thereafter, the mixture was concentrated under reduced pressure to 10 mL and diluted with anhydrous Et$_2$O. The resultant precipitate was collected to yield the title compound as the TFA addition salt (776 mg).

EXAMPLE 6

Hexapeptide Boc-Ala-Gln-Ser(Bzl)-Gly-Leu-Gly-OH (a) Dipeptide H-Leu-Gly-OCH$_3$: DIEA (21 mL) was added to a stirred solution of HCl.H-Gly-OCH$_3$ (13 g) in EtOAc (500 mL). After 15 min, Boc-Leu-OH.H$_{20}$ (20 g) and N-ethoxycarbonyl-2-ethoxy-1,2-dihydroquinoline (25.5 g) were added in succession. The reaction mixture was stirred at room temperature for 18 h, and then filtered. The filtrate was washed serially with H$_{20}$, 1N HCl, H$_{20}$, 5% aqueous NaHCO$_3$ and water. The dried (Na$_2$SO$_4$+MgSO$_4$) organic phase was concentrated to near dryness. Et$_{20}$ was added to the concentrate and the mixture was stored at 4° C. for 18 h. The resultant precipitate was collected and dried to give Boc-Leu-Gly-OCH$_3$ (15.6 g). The latter compound (15.5 g) was dissolved in CH$_2$Cl$_2$ (150 mL) and the solution cooled to 0° C. TFA (60 mL) was added dropwise to the cooled solution. The mixture was stirred at 0° C. for 1.5 h and then evaporated to dryness. TFA was removed from the residue by adding Dowex 1×2-400 ion exchange resin (40 g), prewashed with methanol (4×100 mL), 1N HCl (3×200 mL) and methanol (4×100 mL), to a solution of the crude residue in methanol (300 mL). (Note: Dowex is a trademark). The mixture was stirred at room temperature for 1h and then filtered. The filtrate was concentrated under reduced pressure to give TFA.H-Leu-Gly-OCH$_3$ (17.9 g).

(b) Dipeptide Boc-Ser(Bzl)-Gly-OH: A solution of Boc-Ser(Bzl)-OH (23.6 g) and N-hydroxysuccinimide (9.8 g) in EtOAc (400 mL) was cooled to 0° C. A solution of DCC (71.54 g) in EtOAc (100 mL) was added to the cooled solution. The mixture was stirred at 0° C. for 4 h and then filtered. The collected solid was washed with EtOAc. The filtrate was cooled to 0° C. HCl.H-Gly-OCH$_3$ (10.67 g) and DIEA (42 mL) was added to the cooled solution. The mixture was stirred for 18 h while the temperature of the mixture gradually came to room temperature. The mixture was filtered. The filtrate was concentrated to ca 400 mL, washed serially with H$_2$O, 5% aqueous NaHCO$_3$, 1N HCl and H$_2$O, dried (Na$_2$SO$_4$/MgSO$_4$), and concentrated to dryness. The residual oil was dissolved in Et$_2$O (100 mL). A flocculent precipitate developed which was removed by filtration. The filtrate was concentrated to dryness and dried under reduced pressure to give Boc-Ser(Bzl)-Gly-OCH$_3$ as a colorless oil (28.7 g). A solution of the latter compound (28.0 g) in dioxane (140 mL) and H$_2$O (60 mL) was cooled to 0° C. A solution of NaOH (4.0 g) in H$_2$O (80 mL) was added dropwise to preceding solution. The mixture was stirred at 0° C. during the addition and for 15 min thereafter. The mixture was diluted with H$_2$O and washed with Et$_2$O. The aqueous phase was separated and shaken with EtOAc. Solid citric acid was added to mixture (pH=3-4). The aqueous layer was separated from the EtOAc and extracted with fresh EtOAc. The combined organic extracts were washed with H$_2$O, dried (Na$_2$SO$_4$) and concentrated. The glassy residue was dried under high vacuum to give the dipeptide Boc-Ser(Bzl)-Gly-OH (27.22 g).

(c) Tetrapeptide H-Ser(Bzl)-Gly-Leu-Gly-OCH$_3$: HCl.H-Leu-Gly-OCH$_3$ (12.2 g, 51.3 mmol) was dissolved in DMF (200 mL). DIEA (24 mL, 139.8 mmol) was added to the solution. This first solution was cooled to 0° C. A second solution of Boc-Ser-(Bzl)-Gly-OH (16.42 g, 46.6 mmol) and DPPA (14.1 g, 51.26 mmol) in DMF (122 mL) was added with stirring to the first solution. The mixture was stirred for 20 h while the temperature of the mixture gradually came to room temperature. Concentration of the reaction mixture under reduced pressure gave an oil. The oil was dissolved in EtOAc. The solution was washed with 1N HCl, 1N NaHCO$_3$ and H$_2$O, dried (Na$_2$SO$_4$/MgSO$_4$) and concentrated to dryness to give an oil. Trituration of the latter oil with Et$_2$O-hexane yielded Boc-Ser(Bzl-Gly-Leu-Gly-OCH$_3$ as a solid (23.82 g). The latter compound (28.82 g) was dissolved in 1N HCl in glacial acetic acid (100 mL). The mixture was stirred at room temperature for 1 h and then concentrated under reduced vacuum to give an oil. Trituration of the oil with Et$_2$O afforded the tetrapeptide as a solid (19.71 g, HCl salt).

(d) Pentapeptide H-Gln-Ser(Bzl)-Gly-Leu-Gly-OCH$_3$: The latter tetrapeptide (HCl salt, 8.2 g, 17.34 g mmol) was dissolved in DMF (500 mL) at room temperature. DIEA (9.0 mL, 52 mmol) and Boc-Gln-ONp (7.0 g, 19 mmol) were added to the solution. The mixture was stirred for 20 h and then evaporated to dryness under reduced pressure to give a solid. The solid was stirred with EtOAc for 1 h, collected on a filter, washed with EtOAc, Et$_2$O and hexane, and dried to give Boc-Gln-Ser(Bzl)-Gly-Leu-Gly-OCH$_3$ as a white solid (10.3 g). The amino protecting group (Boc) was removed from the latter compound with 1N HCl in glacial acetic acid in the usual manner, see paragraph (c) of this example, to give HCl.H-Gln-Ser(Bzl)-Gly-Leu-Gly-OCH$_3$ as a solid (9.75 g).

(e) The title compound of this example: DPPA (12.38 g, 45 mmol) was added to a cooled solution (0° C.) of Boc-Ala-OH (3.2 g, 45 mmol) and DIEA (7.8 mL, 45 mmol). The mixture was stirred at 0° C. for 15 min. The pentapeptide from paragraph (d), HCl.H-Gln-Ser(Bzl)-Gly-Leu-Gly-OCH$_3$ (9.0 g, 15 mmol), was added to the mixture. The mixture was stirred for 18 h while the temperature of the mixture gradually came to room temperature. The mixture was concentrated to dryness. The resultant solid was triturated with EtOAc, collected on a filter, and washed with Et$_2$O and then with hexane. The collected solid was suspended in Et$_2$O and the suspension stirred vigorously for 1 h. The solid was collected on a filter and dried to give Boc-Ala-Gln-Ser(Bzl)-Gly-Leu-Gly-OCH$_3$ (10.94 g). The latter compound (6.0 g, 8.15 mmol) was suspended in dioxane (150 mL) and H$_2$0 (200 mL). The suspension was stirred and cooled to 0° C. A solution of NaOH (425 mg, 10.6 mmol) was added dropwise to the cooled suspension. The mixture was stirred at room temperature until it became clear (2 h). The mixture was rendered acidic (pH=4) by the addition of acetic acid and then concentrated under reduced pressure (after addition of isopropanol to prevent foaming). The residue was dissolved in the minimum amount of butanol/H$_2$O/acetic acid (4:5:1). The solution was passed through a column of Sephadex (tradename for a brand of cross linked chains of organic compounds derived from dextran). The pure fractions were combined to give the desired hexapeptide i.e. the title compound of this example, as the HCl addition salt (4.90 g).

EXAMPLE 7

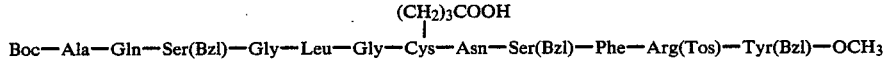
Boc—Ala—Gln—Ser(Bzl)—Gly—Leu—Gly—Cys—Asn—Ser(Bzl)—Phe—Arg(Tos)—Tyr(Bzl)—OCH$_3$ (9: Q=CH$_2$, R$^4$=Phe, R$^7$=Boc, R$^8$=OCH$_3$, R$^{54}$=Tyr(Bzl), R$^{64}$=OH, V$^2$=Bzl, V$^3$=Tos, X=S and Y=CH$_2$)

(a) A solution of the title compound of Example 5 (TFA salt, 700 mg, 0.462 mmol), the title compound of Example 6 (HCl salt, 416 mg, 0.577 mmol), DIEA (0.32 mL, 1.73 mmol) and DPPA (793 mg, 2.88 mmol) in DMF (100 mL) was allowed to stand at −5° C. for 18 h. The solution was concentrated to dryness under reduced pressure. The residue was suspended in EtOAc. The solid material was collected on a filter and washed with Et$_2$O. Repetition of the latter purification treatment, using MeOH instead of EtOAc gave the corresponding FmO ester of the title compound of this example (720 mg).

(b) The latter product (720 mg) was dissolved in DMF (15 mL). The solution was kept at 0° C. while piperidine (5 mL) was added dropwise over a period of 15 min. The reaction mixture was stirred at 0° C. for 40 min and then evaporated to dryness. Addition of EtOAc to the residue caused the formation of a transport precipitate which was collected on a filter and washed with Et$_2$O. The precipitate was suspended in 50 mL of EtOH containing 1 mL of acetic acid. With stirring, the suspension was warmed to 60° C., then cooled to room temperature. The solid was collected on a filter and washed throughly with Et$_2$O to afford the title compound of this example (550 mg).

EXAMPLE 8

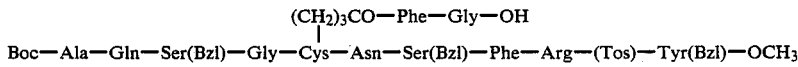
Boc—Ala—Gln—Ser(Bzl)—Gly—Cys—Asn—Ser(Bzl)—Phe—Arg—(Tos)—Tyr(Bzl)—OCH$_3$ (a) Dipeptide H-Phe-Gly-OFm: By following the procedure of Example 1 but replacing 4-bromobutyric acid with Boc-Gly-OH, Boc-Gly-OFm was obtained. The latter compound was transformed to TFA.H-Gly-OFm by treatment with TFA in CH$_2$Cl$_2$ (of the procedure of paragraph (b) of Example 4). Coupling of TFA.H-Gly-OFm with Boc-Phe-OH using DPPA as the coupling agent (of paragraph 9 of Example (4) gave Boc-Phe-Gly-OFm. Treatment of the latter compound with HCl in glacial acetic acid selectively removed the Boc to yield the desired dipeptide (of paragraph (c) of Example 6).

(b) Preparation of title compound of this example: A solution of the title compound of Example 7 (540 mg, 0.26 mmol), the preceding dipeptide H-Phe-Gly-OFm (453 mg, 104 mmol), DPPA (357 mg, 1.3 mmol) and DIEA (0.5 mL) in DMF (50 mL) was allowed to stand at 0° C. for 2 hr and then at 4° C. for 20 h. The reaction mixture was worked up in the same manner as described for the reaction mixture of Example 7, paragraph (a), to give the 9-fluorenylmethyl ester (at the terminal Gly) of the title compound (510 mg).

Treatment of the latter compound with piperidine in DMF in the same manner as described in paragraph (b) of Example 7 gave the title compound (400 mg).

EXAMPLE 9

Heptapeptide
H-Gly-Arg(Tos)-Ile-Asp(Chxl)-Arg(Tos)-Ile-Gly-

OFm (a) Dipeptide Boc-Arg(Tos)-Ile-OH: DIEA (19 mL, 106.5 mmol) and HOBt (5.08 g, 37.63 mmol) were added at room temperature to a solution of Boc-Arg(Tos)-OH (16.13 g, 37.64 mmol) and TFA.H-Ile-OFm (15 g, 35.5 mmol) in anhydrous DMF (100 mL). The resulting mixture was diluted with CH$_2$Cl$_2$ (300 mL) and cooled to 0° C. A solution of DCC (7.76 g) in 30 mL of CH$_2$Cl$_2$ was added to the cooled mixture. The mixture was stirred for 18 h while the temperature of the mixture gradually came to room temperature. The mixture was filtered. The filtrate was concentrated under reduced pressure. The residual oil was dissolved in EtOAc. The solution was washed with H$_2$O, 1N HCl, 5% aqueous NaHCO$_3$ and H$_2$O, dried (Na$_2$SO$_4$/MgSO$_4$), and concentrated to yield Boc-Arg(Tos)-Ile-OFm as a white solid (22.42 g). The latter compound (22.0 g) was dissolved in DMF (200 mL). Piperidine (40 mL) was added dropwise to the solution. The reaction mixture was stirred at room temperature for 2 h and thereafter concentrated to dryness under reduced pressure. The residue was dissolved in EtOAc. The solution was washed with aqueous citric acid solution (pH 4). The aqueous phase was extracted with fresh EtOAc. The combined EtOAc solutions were washed with 1N HCl and H$_2$O, dried (Na$_2$SO$_4$/MgSO$_4$), and concentrated to dryness. The residue was rinsed with hexane and then dissolved in warm EtOAc. After filtration to remove insoluble material, the EtOAc solution was diluted with hexane. The resulting precipitate was collected to give the dipeptide (17.6 g).

(b) Tripeptide H-Arg(Tos)-Ile-Gly-OFm: The latter dipeptide (14.81 g, 27.3 mmol) was dissolved in DMF (75 mL). TFA.H-Gly-OFm (10.0 g, 27.3 mmol), DIEA (14.3 mL, 81.9 mmol) and HOBt (3.69 g, 27.3 mmol) were added to the solution. The mixture was diluted with CH$_2$Cl$_2$ (225 mL) and cooled to 0° C. A solution of DCC (5.63 g, 27.3 mmol) in 25 mL of CH$_2$Cl$_2$ was added to the mixture. The mixture was stirred for 18 h while the temperature of the mixture was allowed to rise to room temperature. The reaction mixture was worked up to the same manner as described for Boc-Arg(Tos)-Ile-OFm in the preceding paragraph, except that the product obtained following the washings was purified by chromatography on silica gel, using EtOAc-hexane (1:1) as eluent, to give Boc-Arg(Tos)-Ile-Gly- OFm (13.2 g). The Boc protecting group was removed from the latter compound (13.0 g) with 1N HCl in glacial acetic acid, of Example 6 (c), to give the desired tripeptide as its HCl addition salt (12.0 g).

(c) Dipeptide H-Ile-Asp(Chxl)-OFm: Boc-Ile-OH.1/2H₂O (32.72 g, 136.8 mmol) was dissolved in CH₂Cl₂ (200 mL) and the solution cooled to 0° C. A cold solution (0° C.) of DCC (14.11 g, 68.4 mmol) in CH₂Cl₂ (100 mL) was added in one portion to the preceding solution. The mixture was stirred at 0° C. for 1 and then filtered. DIEA (24 mL, 136.8 mmol) was added to the filtrate, followed by an addition of TFA.H-Asp(Chzl)-OFm (22.37 g, 45.6 mmol). The mixture was stirred at 0° C. for 1 h, allowed to stand at room temperature for 20 h, and then concentrated to dryness. The oily residue was dissolved in EtOAc. The solution was washed with H₂O, 1N HCl, 5% aqueous NaHCO₃ and water, dried (Na₂SO₄) and concentrated to yield Boc-Ile-Asp-(Chxl)-OFm as a foam (31.86 g). The latter compound (26.9 g) was deblocked, i.e. the amino protecting group was removed, with TFA in CH₂Cl₂, of paragraph (b) of example 4, to give the dipeptide as its HCl addition salt (22.63 g).

(d) Tetrapeptide Boc-Gly-Arg(Tos)-Ile-Asp(Chxl)-OH: The latter dipeptide (HCl salt 22.63 g, 41.24 mmol) was coupled with Boc-Arg(Tos)-OH (17.67 g, 41.24 mmol), using DPPA as the coupling agent, according to the procedure of Example 4, paragraph (a), to give Boc-Arg(Tos)-Ile-Asp(Chx)-OFm (34.0 g). The latter compound was deblocked with TFA in CH₂Cl₂ to give the tripeptide TFA.H-Arg(Tos)-Ile-Asp)Chxl-OFm. Subsequent coupling of the latter compound with Boc-Gly-OH to obtain Boc-Gly-Arg(Tos)-Ile-Asp-(Chxl)-OFm (15.69 g), according to the preceding coupling procedure, followed by treatment of the latter product with piperidine in DMF (of paragraph (a) of this example) gave the tetrapeptide Boc-Gly-Arg(Tos)-Ile-Asp(Chxl)-OH (12.35 g).

(e) Title compound of this example: Finally, by coupling the latter tetrapeptide (12.35 g, 15.83 mmole) with the tripeptide HCl.H-Arg(Tos)-Ile-Gly-OFm of paragraph (b) of the example (12.0 g, 16.85 mmol), according to the procedure of Example 4, paragraph (a), the title compound of the example was obtained as a white powder (TFA salt, 18.0 g).

EXAMPLE 10

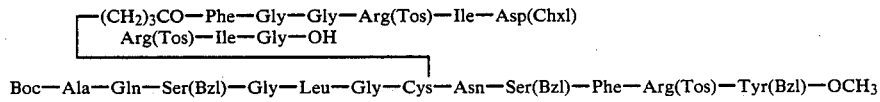

(11: Q=CH₂, R¹ and R⁴=Phe, R²=Gly, R⁸=OCH₃, R³ᴬ=Ile, R⁵ᴬ=Tyr(Bzl), V²=Bzl, V³=Tos, V⁴=Chxl, X=S and Y=CH₂)

A solution of the title compound of example 8 (400 mg, 0.19 mmol), the title compound of example 9 (TFA salt, 580 mg, 0.40 mmol), DIEA (0.2 mL) and DPPA (550 mg, 2 mmol) in DMF (50 mL) was allowed to stand at −5° C. for 24 h. The reaction mixture was worked up in the same manner as described in the first paragraph of example 7 to give the corresponding 9-fluorenylmethyl ester of the title compound (390 mg).

Treatment of the latter compound with piperidine in the same manner as described in the second paragraph of Example 7 gave the title compound (390 mg).

EXAMPLE 11

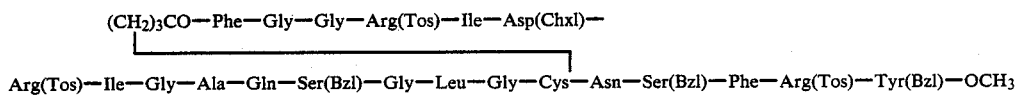

(12: Q=CH₂, R¹ and R⁴=Phe, R²=Gly, R⁸=OCH₃, R³ᴬ=Ile, R⁵ᴬ=Tyr(Bzl), V²=Bzl, V³=Tos, V⁴=Chxl, X=S and Y=CH₂)

A suspension of the title compound of Example 10 (380 mg) in CH₂Cl₂ (10 mL) was kept at 0° C. while TFA (10 mL) was added dropwise. The reaction mixture was allowed to stand at 0° C. for 30 min. Thereafter, the reaction mixture was concentrated to dryness under reduced vacuum. The residue was suspended in Et₂O. The resulting solid was collected by filtration and washed with Et₂O to afford the corresponding amino deprotected compound of the title compound of example 10 as the TFA salt (320 mg), i.e. the corresponding compound in which the Boc has been removed.

The latter compound (320 mg) was dissolved in DMF (100 mL). The solution was added by peristaltic pump to a cooled solution (−5° C.) of DIEA (320 µL) and DPPA (1 mL). The reaction mixture was allowed to stand at −5° C. for 48 h and then concentrated under reduced pressure. The residue was suspended in EtOAc. The resulting solid was collected and washed with Et₂O to afford the title product (260 mg).

EXAMPLE 12

Peptide of formula 1 (Q=CH₂, R¹=Phe, R²=Gly, R³=Ile, R⁴=Phe, R⁵=Tyr, X=S, Y=CH₂ and W=OCH₃) having the formula

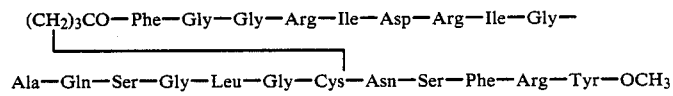

The title compound of example 11 (260 mg) was stirred with anhydrous hydrogen fluoride (16 mL), anisole (2.0 mL) and ethanedithiol (0.5 mL) at −15° C. for 30 min, followed by stirring at 0° C. for 45 min. The reaction mixture was concentrated under reduced pressure. The residue distributed between Et$_2$O and H$_2$O and the mixture was shaken. The Et$_2$O layer was separated and the aqueous phase extracted with fresh Et$_2$O.

The aqueous layer was subjected to reduced pressure to remove residual Et$_2$O therein and then lyophilized to give the crude title compound (170 mg). Purification of the crude material was effected by reversed phase chromatography on a octade-casilyl-silica column (4×30 cm, C-18, Vydac, 30 μ particle size) using a gradient of 0–70% methanol in 0.1% aqueous TFA. The fractions comprising the major peptide peak (UV detection at 230 nm) were pooled and lyophilized. Repetition of reversedphase chromatography procedure using a column having a particle size of 15–20 μ gave the pure title compound; amino acid analysis: Asp+Asn (2.01), Ser (1.85), Gln (1.00), Gly (5.21), Ala (1.03), Ile (1.82), Leu (0.99), Tyr (0.90), Phe (2.00), Arg (3.20); FAB MS C$_{103}$H$_{158}$N$_{32}$O$_{30}$S requires 2356.6; found, 2357M+.

EXAMPLE 13

By following the procedure of Example 4 to 12, but using N-(t-butyloxycarbonyl)-S-[3-(9-fluorenylmethoxy)-3-oxopropyl]-L-homocysteine, N-(t-butylloxycarbonyl)-0-[4-(9-fluorenylmethoxy)-4-oxobutyl]-L-serine or N-(benzyloxycarbonyl)-0-([3-(9-fluorenylmethoxy)-3-oxopropyl]-L-homoserine as the starting material of formula 2, the following peptides of formula 1 are obtained: rat [(CH$_2$CH$_2$CO)$^{105}$, hCys$^{121}$]ANF-(105-126)OCH$_3$, [(CH$_2$CH$_2$CO)$^{105}$, Ser$^{121}$]ANF-(105-126) OCH$_3$ and rat [(Ch$_2$CH$_2$CO)$^{105}$, hSer$^{121}$]ANF-(105-126)OCH$_3$, respectively.

EXAMPLE 14

By following the procedure of Examples 5 to 12, but replacing the pentapeptide H-Asn-Ser(Bzl)-Phe-Arg(Tos)-Tyr(Bzl)-OCH$_3$ with the pentapeptide H-Asn-Ser(Bzl)-Phe-Arg(Tos)-Tyr(Bzl)-NH$_2$, the peptide of formula 1, rat [(CH$_2$CH$_2$CH$_2$CO)$^{105}$)-ANF-(105]-126)NH$_2$, is obtained.

EXAMPLE 15

By following the procedure of Examples 5 to 12, but replacing the pentapeptide H-Asn-Ser(Bzl)-Phe-Arg(Tos)-Tyr(Bzl)-OCH$_3$ with the pentapeptide H-ASN-Ser(Bzl)-Phe-Arg(Tos)Tyr(Bzl)-OBzl, rat [(CH$_2$-CH$_2$CH$_2$CO)$^{105}$]ANF-(105-126) is obtained. Amino acid analysis of the product (1, Q=CH$_2$, R$^1$=Phe, R$^2$=Gly, R$^3$=Ile, R$^4$=Phe, R$^5$=Tyr, X=S, Y=CH$_2$ and W=OCH$_3$) gave Asp+Asn (2.03), Ser (1.84), Gln (1.03), Gly (5.08), Ala (1.04), Ile (1.77), Leu (1.06), Tyr (0.96), Phe (2.00), Arg (3.16). Molecular weight was determined by FAB mass spectroscopy: C$_{102}$H$_{156}$N$_{32}$O$_{30}$S requires 2342; found, 2342M+.

EXAMPLE 16

By following the procedure of Example 5 to 12, but replacing N-(t-butyloxycarbonyl)-S-(4-(9-fluorenylmethoxy)-4-oxobutyl)-L-cysteine with N-(t-butyloxycarbonyl)-S-(4-(9-fluorenylmethoxy) -4-oxo-butyl)-L-penicillamine, and replacing the pentapeptide H-Asn-Ser(Bzl)-Phe-Arg(Tos)-Tyr(Bzl)-OCH$_3$ with H-Asn-Ser(Bzl)-Phe-Arg(Tos)-Tyr(Bzl)-OBzl, rat[(CH$_2$CH$_2$CH$_2$CO)$^{105}$, Pen$^{121}$]-ANF(105-126) is obtained. Amino acid analysis of the product (1, Q=C(CH$_3$)$_2$, R$^1$=Phe, R$^2$=Gly, R$^3$=Ile, R$^4$=Phe, R$^5$=Tyr, X=S, Y=CH$_2$ and W=OH) gave Asp+Asn (1.91), Ser (1.91), Gln (1.02), Gly (5.16), Ala (0.98), Ile (1.76), Leu (1.10 ), Tyr (0.97), Phe (2.00). Molecular weight was determined by FAB mass spectroscopy: C$_{104}$H$_{106}$N$_{32}$O$_{30}$S requires 2.369.6; found, 2370M+.

EXAMPLE 17

By following the procedure of Examples 5 to 12, but replacing N-(t-butyloxycarbonyl)-S-(4-(9-fluorenylmethoxy)-4-oxobutyl-L-cysteine with N-(t-butyloxycarbonyl)-S-(3-(9-fluorenylmethoxy)-3-oxopropyl-L-homocysteine, and replacing H-Asn-Ser(Bzl)-Phe-Arg(Tos)-Tyr(Bzl)-OCH$_3$ with H-Asn-Ser(Bzl)-Phe-Arg(Tos)-Tyr(Bzl)-OBzl, rat[(CH$_2$CH$_2$CO)$^{105}$, hCys$^{12-1}$]ANF-(105-126) is obtained Amino acid analysis of the product (1,Q=CH$_2$CH$_2$, R1=Phe, R$^2$=Gly, R$^3$=Ile, R$^4$=Phe, R$^5$=Tyr, X=S, Y$^1$des-Y and W is hydroxy) gave Asn+Asp (2.00), Ser (1.78), Gln (1.01), Gly(5.18), Ala (1.00), Ile (1.80), Leu (1.02), Tyr (0.99), Phe (2.00), Arg (3.45). Molecular weight was determined by FAB mass spectroscopy: C$_{102}$H$_{156}$N$_{32}$O$_{30}$ S requires 2342.6: found, 2342M+.

Examples of other peptides of formula 1, which are prepared by the same general procedures described herein, are as follows:

rat [(CH$_2$CH$_2$CH$_2$CO)$^{105}$,4FPhe$^{106}$]ANF-(105-126),
rat [(CH$_2$CH$_2$CH$_2$CO)$^{105}$, hCys$^{121}$)ANF-(105-126),
human [(CH$_2$CH$_2$CO)$^{105}$,hSer$^{121}$,4CF$_3$Phe$^{124}$]ANF 125)NH(C$_2$H$_5$),
rat[(CH$_2$CH$_2$CH$_2$CO)$^{105}$,4FPhe$^{106}$,D-Ala$^{107}$]ANF-(105-125),
rat [(CH$_2$CH$_2$CH$_2$CO)$^{105}$,4FPhe$^{106}$,D-Ala$^{107}$]ANF-(105-125) NH$_2$, and
human [(CH$_2$CH$_2$CO)$^{105}$,Ala$^{107}$,Ser$^{121}$]ANF-(105-126)NH2.

We claim:

1. A peptide of formula 1

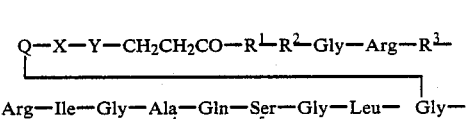

Asp—Arg—Ile—Gly—Ala—Gln—Ser—Gly—Leu— Gly—
NHCHCO—Asn—Ser—R$^4$—Arg—R$^2$—W wherein
Q is methylene, ethylene or CR'R" wherein R' and R" each independently lower alkyl;
R$^1$ and R$^4$ each independently is Phe, 2FPhe, 3FPhe, 4FPhe, 2CF$_3$Phe, 3CF$_3$Phe or 4CF$_3$Phe;
R$^2$ is Gly, Ala or D-Ala;
R$^3$ is Ile or Met;
R$^5$ is Tyr or des-R$^5$;
X is oxy or thio;
Y is methylene or des-Y; and
W is hydroxy, lower alkoxy, amino or lower alkylamino;
with the proviso that when Q is CR'R" as defined herein, then X is thio;
or a therapeutically acceptable salt thereof.

2. A peptide of formula 1 of claim 1 where R$^1$ and R$^4$ each independently is Phe, 2FPhe, 3FPhe or 4FPhe, and W is hydroxy, lower alkoxy or amino; or a therapeutically acceptable salt thereof.

3. A peptide of formula 1 of claim 1 wherein Q is methylene, ethylene, or C(CH$_3$)$_2$, R$^1$ and R$^4$ each independently is Phe, 2FPhe or 4FPhe, X is thio, Y is methylene or des-Y, and W is hydroxy or lower alkoxy; or a therapeutically acceptable salt thereof.

4. A peptide of formula 1 of claim 3 wherein Q is methylene or C(CH$_3$)$_2$ and Y is methylene; or a therapeutically acceptable salt thereof.

5. A peptide formula 1 of claim 3 wherein Q is ethylene and Y is des-Y; or a therapeutically acceptable salt.

6. A peptide of formula 1 of claim 4 wherein Q is methylene or C(CH₃)₂, R¹ is Phe, R² is Gly, R³ is Ile, R⁴ is Phe, R⁵ is Tyr, X is thio, Y is methylene and W is hydroxy or methoxy; or a therapeutically acceptable salt thereof.

7. A peptide of formula 1 of claim 5 wherein Q is ethylene, R¹ is Phe, R² is Gly, R³ is Ile, R⁴ is Phe, R⁵ is Tyr, X is thio, Y: is des-Y and W is hydroxy; or a therapeutically acceptable salt thereof.

8. A peptide of formula 1 of claim 6 wherein Q is methylene; or a therapeutically acceptable salt thereof.

9. A peptide of formula 1 of claim 6 wherein Q is C(CH₃)₂ and Y is hydroxy; or a therapeutically acceptable salt thereof.

10. A pharmaceutical composition which comprises a peptide of claim 1, or a therapeutically acceptable salt thereof, and a pharmaceutically acceptable carrier.

11. A pharmaceutical composition which comprises a peptide of claim 3, or a therapeutically acceptable salt thereof, and a pharmaceutically acceptable carrier.

12. A method of causing a vasorelaxant, diuretic or antihypertensive response in a mammal in need of the response which comprises administering to the mammal an effective amount of the peptide of formula 1 of claim 1 or a therapeutically acceptable salt thereof.

13. A method of treating edematous conditions in a mammal which comprises administering thereto an effective amount of the peptide of formula 1 of claim 1 or a therapeutically acceptable salt thereof.

14. A process for preparing a peptide of formula 1 of claim 1 which comprises deprotecting the cyclic intermediate of formula 12

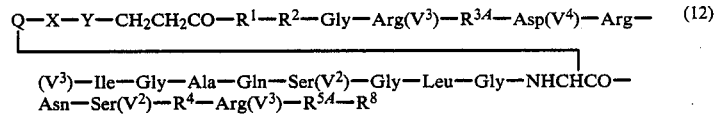
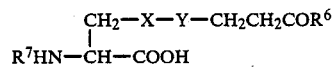

wherein Q, R¹, R², R⁴, X and Y are as defined in claim 1, R⁸ is O-V wherein V is a carboxyl protective group, lower alkoxy, amino or lower alkylamino, R³ᴬ is Ile, Met or Met(O), R⁵ᴬ is des-R⁵ᴬ or Tyr(V¹) wherein V¹ is a protecting group, and V² and V³ are protecting groups and V⁴ is a protecting group selected from cyclohexyl and cyclopentyl to obtain the corresponding peptide of formula 1, and if desired transforming the peptide of formula 1 into a therapeutically acceptable salt.

15. A process of claim 14 wherein the cyclic intermediate is formed by
(a) progressively coupling the appropriate peptidyl fragments to a series of intermediates, beginning with the starting material of formula 2

$$CH_2-X-Y-CH_2CH_2COR^6 \atop R^7HN-CH-COOH \qquad 2$$

wherein R⁶ is a carboxyl protecting group, R⁷ is an amino protecting group, and X and Y are an defined in claim 14 to obtain a branched intermediate of formula 11

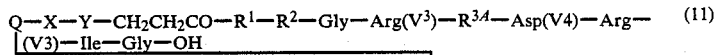
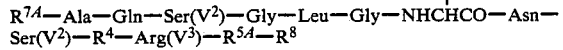

wherein Q, R¹, R², R⁴, X,Y, R⁸, R³ᴬ, R⁵ᴬ, V², V³, and V⁴ are as defined in claim 14 and R⁷ᴬ is hydrogen; and
(b) cyclizing (intramolecular coupling) the branched intermediate of formula 11 with a coupling agent to give the cyclic intermediate of formula 12.

* * * * *